US006194638B1

(12) United States Patent
Dhugga et al.

(10) Patent No.: US 6,194,638 B1
(45) Date of Patent: Feb. 27, 2001

(54) ALTERATION OF HEMICELLULOSE CONCENTRATION IN PLANTS

(75) Inventors: Kanwarpal S. Dhugga; Scott E. Nichols, both of Johnston; Patricia Lynne Fallis, Polk City, all of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/338,671

(22) Filed: Jun. 22, 1999

Related U.S. Application Data

(60) Provisional application No. 60/090,416, filed on Jun. 23, 1998.

(51) Int. Cl.[7] ............................ C12N 5/04; C12N 15/82; C12N 15/29; C12N 15/52; A01H 5/00

(52) U.S. Cl. .................... 800/284; 435/69.1; 435/320.1; 435/419; 435/468; 536/23.2; 536/24.1; 536/23.6; 536/56; 536/24.5; 800/286; 800/278; 800/295; 800/298; 800/305; 800/306; 800/312; 800/314; 800/315; 800/317.1; 800/317.4; 800/320; 800/320.1; 800/320.2; 800/320.3

(58) Field of Search .......................... 536/23.6, 56, 24.5, 536/23.2, 24.1; 800/290, 286, 284, 298, 305, 306, 312, 314, 315, 317.1, 317.4, 320, 320.1, 320.2, 320.3, 278, 295; 435/69.1, 320.1, 419, 468

(56) References Cited

FOREIGN PATENT DOCUMENTS

WO 93/17101 * 9/1993 (GB) .................................. 800/284
WO 94/04693 * 3/1994 (WO) .................................. 800/284

OTHER PUBLICATIONS

Singh et al., "β–Glucosylarginine: a new glucose–protein bond in a self–glucosylating protein from sweet corn", FEBS Letters 376, 61–64 (1995).

Whistler, R.L., "Hemicelluloses", Industrial Gums, Third Edition, Chapter 11, pp. 295–308 (1993).

Sasaki et al. Accession No. D40369, Nov. 1994.*

Dhugga et al., "Plant Polypeptides Reversibly Glycosylated by UDP–Glucose", *The Journal of Biological Chemistry*, vol. 266, No. 32, pp. 21977–21984 (1991).*

Dhugga et al. A reversibly glycosylated polypeptide (RGP) possibly involved in plant cell wall synthesis: Purification, gene cloning, and trans–Golgi Iocalization. Proc. Natl. Acad. Sci. vol. 94, pp. 7670–7684, Jul. 1997.*

Delgado et al. Plant Physiology vol. 116:1339–1349, Apr. 1998.*

Epel et al. Protoplasma 191:70–78, 1996.*

Katz et al. EMBL Accession No. AF005278, May 1997.*

* cited by examiner

*Primary Examiner*—David T. Fox
*Assistant Examiner*—Medina A Ibrahim
(74) *Attorney, Agent, or Firm*—Pioneer Hi-Bred International, Inc.

(57) ABSTRACT

The invention provides isolated Rgp nucleic acids and their encoded proteins. The present invention provides methods and compositions relating to altering RGP levels in plants. The invention further provides recombinant expression cassettes, host cells, transgenic plants, and antibody compositions.

20 Claims, No Drawings

ALTERATION OF HEMICELLULOSE CONCENTRATION IN PLANTS

This application claims priority under 35 USC 119(e) to provisional application 60/090,416 filed Jun. 23, 1998.

TECHNICAL FIELD

The present invention relates generally to plant molecular biology. More specifically, it relates to nucleic acids and methods for modulating their expression in plants.

BACKGROUND OF THE INVENTION

The disclosure of U.S. Ser. No. 60/090,416 is hereby incorporated by reference.

Mature plant cell walls generally contain about 30–40% hemicellulose. Hemicellulose in monocot walls consists mainly of arabinoxylan (also referred to as glucurono-arabinoxylan or pentosans), a branched polymer consisting of β-gylosyl backbone decorated with arabinosyl and glucuronosyl residues. This polymer is often referred to as arabinoxylan because of the relatively low proportion of glucuronosyl residues. Carpita, N. C., "Structure and Biogenesis of the Cell Walls of Grasses" *Annual Review of Plant Physiol. and Plant Molecular Biology* 476:445–476 (1996).

Dicot cell walls, in contrast, contain xyloglucan as the main hemicellulosic polymer. Xyloglucan is also a branched polymer consisting of a linear β-glycosyl backbone which is decorated with xylosyl residues, some of which residues are substituted with galactosyl residues.

Cell walls of corn grain constitute about 6–8% of the total dry weight for both coarse and fine fiber. Whistler, R. L. et al, *Hemicelluloses In Industrial Gums: Polysaccharides and Their Derivatives,* San Diego: Academic Press, pp. 295–308 (1993). The grain cell wall contains 45–65% arabinoxylan, the remainder being mainly cellulose. Under certain circumstances it would be advantageous to reduce the concentration of arabinoxylan in the grain cell wall.

Arabinoxylans are considered to be anti-nutritional components of animal feed. This is because they can absorb large amounts of water, leading to increased viscosity and possible sequestering of other digestible feed components, such as starch and proteins, away from digestive enzymes. Arabinoxylans are also known to lower the food conversion ratio (FCR). In studies where fungal xylanase is included in cereal-derived feed, improved FCR and weight gain in broilers and pigs (Veldman and Vahl, H. A., "Xylanase in broiler diets with differences in characteristics and content of wheat" *British Poultry Science* 35:537–550 (1994). The improvement observed for FCR and weight gain is higher than can be expected from arabinoxylan breakdown and digestion alone. Thus, arabinoxylan appears to reduce the digestion of other feed components. Therefore, it would be desirable to reduce the concentration of arabinoxylan in grain.

Cellulose microfibrils have the highest tensile strength of any of the other cell wall polymers. Increasing the cellulose/arabinoxylan ratio in the cell wall should lead to a harder pericarp and improved handling ability of the grain.

About 12% of the corn processed through wet-milling is fiber. Of this 12%, approximately 4% is coarse fiber (mainly pericarp-derived) and the rest is fine fiber. Whereas the coarse fiber consists of approximately 9% starch, fine fiber can have up to 30% starch which constitutes 2.5% of the total dry mass. The other major fraction of fine fiber is arabinoxylan which makes up to 21% of this fraction. It is likely that some of the starch becomes intricately associated with arabinoxylan, thereby making it difficult to extract during wet-milling. Thus, the need arises for a method to reduce the concentration of arabinoxylan in grain to improve starch extractibility.

Under other circumstances, it is desirable to increase the concentration of arabinoxylan in grain. Dietary fiber in grains from a number of plant species grown for human consumption has been shown to reduce cholesterol and low density lipoprotein levels in the plasma. Corn soluble fiber (arabinoxylan) has been shown to be superior to that of wheat in rats in lowering cholesterol levels. In the case of crops such as corn, grown for human consumption, it would therefore be desirable to increase the arabinoxylan content.

There are markets for isolated arabinoxylan preparations for various industrial use, i.e., as thickeners, emulsifiers or stabilizers in food, cosmetics, and pharmaceuticals. Whistler, supra. Increasing the concentration of arabinoxylan in corn grain targeted for wet-milling would make the process of arabinoxylan isolation more economical.

Finally, the modulation of hemicellulose content can be utilized to control plant growth. For example, plant growth is determined by concerted synthesis of cell wall polymers. It is expected that increased synthesis of one of the cell wall polymers, such as hemicellulose, will cause an increase in the synthesis of the rest of the polymers as well. It is expected that increased production of arabinoxylan or xyloglucan in vegetative tissue will accelerate plant growth. In contrast, it is expected that decreased production of arabinoxylan or xyloglucan will inhibit the synthesis of other cell wall polymers. In this regard, reduced production of arabinoxylan will slow plant growth. Additionally, tissue-specific control of hemicellulose productivity is used to modify plant organ growth and development. Early flowering, larger fruit size, or stronger stalk or stem quality is achieved by operably linking a tissue specific promoter to an Rgp gene the expression of which increases hemicellulose biosynthesis.

In view of the foregoing, it would be desirable to modulate the arabinoxylan and xyloglucan concentration in crop plants.

SUMMARY OF THE INVENTION

Generally, it is the object of the present invention to provide nucleic acids and proteins relating to hemicellulose production. It is an object of the present invention to provide: 1) antigenic fragments of the proteins of the present invention; 2) transgenic plants comprising the nucleic acids of the present invention; 3) methods for modulating, in a transgenic plant, the expression of the nucleic acids of the present invention.

It is another object of the present invention to provide methods for decreasing the concentration of arabinoxylan in the grain of a crop plant.

It is yet another object of the present invention to provide methods for producing livestock feed grain with a higher feed conversion ratio.

It is yet another object of the present invention to provide methods for improving feed grain handling quality.

It is yet another object of the present invention to provide methods for producing grain with improved starch extractibility.

It is an object of the present invention to provide methods for increasing the concentration of arabinoxylan in the grain of a crop plant.

It is yet another object of the present invention to provide methods for producing grain for human comsumption with a reduced caloric content.

It is yet another object of the present invention to provide methods for producing grain for human consumption with an increased soluble fiber content.

It is yet another object of the present invention to provide plants with improved stalk or stem quality.

It is yet another object of the present invention to provide plants with altered growth rates to affect flowering.

Therefore, in one aspect, the present invention relates to an isolated nucleic acid comprising a member selected from the group consisting of:

(a) a polynucleotide that encodes a polypeptide of SEQ ID NOS 2 or 4;

(b) a polynucleotide amplified from a plant tissue nucleic acid library using the primers of SEQ ID NOS 5 and 6, or, 7 and 8;

(c) a polynucleotide comprising at least 20 contiguous bases of SEQ ID NOS 1 and 3;

(d) a polynucleotide encoding plant RGP polypeptides;

(e) a polynucleotide having at least 60% sequence identity to SEQ ID NOS 1 or 3:, wherein the % sequence identity is based on the entire coding sequence and is determined by BLAST 2.0 under default parameters;

(f) a polynucleotide comprising at least 25 nucleotides in length which hybridizes under stringent conditions to a polynucleotide having the sequence set forth in SEQ ID NOS 1 and 3, wherein the conditions include a wash with 0.1X SSC at 60° C.;

(g) a polynucleotide comprising the sequence set forth in SEQ ID NOS 1 and 3; and (h) a polynucleotide complementary to a polynucleotide of (a) through (g).

The isolated nucleic acid can be DNA.

In another aspect, the present invention relates to recombinant expression cassettes, comprising a nucleic acid of the present invention operably linked to a promoter in sense or antisense orientation.

In another aspect, the present invention is directed to a host cell into which has been introduced the recombinant expression cassette.

In a further aspect, the present invention relates to an isolated protein comprising a polypeptide having a specified number of contiguous amino acids encoded by an isolated nucleic acid of the present invention.

In yet another aspect, the present invention relates to a transgenic plant comprising a recombinant expression cassette comprising a plant promoter operably linked to any of the isolated nucleic acids of the present invention. In some embodiments, the transgenic plant is *Zea mays*. The present invention also provides transgenic seed from the transgenic plant.

In yet another aspect, the present invention relates to a method for modulating the level of RGP in a plant, comprising:

(a) stably transforming a plant cell with an Rgp polynucleotide operably linked to a promoter, wherein the polynucleotide is in sense or antisense orientation; and (b) growing the plant cell under plant growing conditions to produce a regenerated plant capable of expressing the polynucleotide for a time sufficient to modulate the level of reversibly glycosylated protein in the plant.

In yet another aspect, the present invention relates to a method for modulating the level of arabinoxylan in a plant, comprising:

(a) stably transforming a plant cell with an Rgp polynucleotide operably linked to a promoter, wherein the polynucleotide is in sense or antisense orientation; and (b) growing the plant cell under plant growing conditions to produce a regenerated plant capable of expressing the polynucleotide for a time sufficient to modulate level of arabinoxylan in the plant.

In yet another aspect, the present invention relates to a method for modulating the level of xyloglucan in a plant, comprising:

(a) stably transforming a plant cell with an Rgp polynucleotide operably linked to a promoter, wherein the polynucleotide is in sense or antisense orientation; and (b) growing the plant cell under plant growing conditions to produce a regenerated plant capable of expressing the polynucleotide for a time sufficient to modulate level of xyloglucan in the plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications,* D. H. Persing et al., Ed., American Society for Microbiology, Washington, D.C. (1993). The product of amplification is termed an amplicon.

The term "antibody" includes reference to antigen binding forms of antibodies (e.g., Fab, $F(ab)_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech.* 14: 309–314 (1996).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum,* or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al., *Nucl. Acids Res.* 17: 477–498 (1989)). Thus, the maize preferred codon for a particular amino acid may be derived from known gene sequences from maize. Maize codon usage for 28 genes from maize plants is listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology. A Laboratory Manual,* Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli,* or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual,* Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or produced by non-natural, synthetic, methods, or if it is transcribed from DNA which has been altered, by non-natural, synthetic methods. The isolated nucleic acid may also be produced by the synthetic re-arrangement ("shuffling") of a part or parts of one or more allelic forms of the gene of interest. Likewise, a naturally occurring nucleic acid (e.g., a promoter) becomes isolated if it is introduced to a locus of the genome not native to that nucleic acid. Nucleic acids which are "isolated" as defined herein, are also referred to as "heterologous" nucleic acids.

Unless otherwise stated, the term "Rgp nucleic acid" is a nucleic acid of the present invention and means a nucleic acid comprising a polynucleotide of the present invention (an "Rgp polynucleotide") encoding an RGP polypeptide. An "Rgp gene" is a gene of the present invention and refers to a heterologous genomic form of a full-length Rgp polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to *Molecular Cloning Techniques, Methods in Enzymology,* Vol. 152, Academic Press, Inc., San Diego, Calif. (Berger); Sambrook et al., *Molecular Cloning—A Laboratory Manual,* 2nd ed., Vol. 1–3 (1989); and Current Protocols in Molecular Biology, F. M. Ausubel et al, Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. Preferred plants are: corn, soybean, sunflower, sorghum, canola, wheat, alfalfa, cotton, rice, barley, millet or Arabidopsis thaliana, tomato, Brassica vegetables, peppers, potatoes, apples, spinach, or lettuce.

A particularly preferred plant is *Zea mays.*

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "RGP polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. An "RGP protein" is a protein of the present invention and comprises an RGP polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodies, A Laboratory Manual,* Cold Spring Harbor Publications, New York (1988), for a description of immunoassay formats and conditions that can be used to determine selective reactivity.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1X to 2X SSC (20X SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5X to 1X SSC at 55 to 60° C. Exemplary high stringency conditions include hybridization in 50% formamide, 1 M NaCl, 1% SDS at 37° C., and a wash in 0.1X SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl, *Anal. Biochem.,* 138:267–284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. Tm is reduced by about 1° C. for each 1% of mismatching; thus, $T_m$, hybridization and/or wash conditions can be adjusted to hybridize to sequences of the desired identity. For example, if sequences with ≧90% identity are sought, the Tm can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes,* Part 1, Chapter 2 "Overview of principles of hybridization and the strategy of nucleic acid probe assays", Elsevier, New York (1993); and *Current Protocols in Molecular Biology,* Chapter 2, Ausubel, et al., Eds., Greene Publishing and Wiley-lnterscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", and (d) "percentage of sequence identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8: 155–65 (1992), and Pearson, et al., *Methods in Molecular Biology* 24: 307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology,* Chapter 19, Ausubel, et al., Eds., Greene Publishing and Wiley-lnterscience, New York (1995).

Unless otherwise stated, sequence identity/similarity values provided herein refer to the value obtained using the BLAST 2.0 suite of programs using default parameters. Altschul et al., *Nucleic Acids Res.* 25:3389–3402 (1997). Software for performing BLAST analyses is publicly available, e.g., through the National Center for Biotechnology Information (hftp://www.ncbi.nim.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci.* USA 89:10915).

In addition to calculating percent sequence identity, the BLAST algorithm also performs a statistical analysis of the similarity between two sequences (see, e.g., Karlin & Altschul, *Proc. Nat'l. Acad. Sci.* USA 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149–163 (1993)) and XNU (Claverie and States, *Comput. Chem.,* 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

DETAILED DESCRIPTION OF THE INVENTION

Overview

With the exception of cellulose, which is synthesized at the plasma membrane, other cell wall polysaccharides, including those involved in the formation of hemicellulose, are first synthesized in the Golgi and then exported to the cell wall by exocytosis Ray et al., *Ber. Deutsch Bot. Ges. Bd.* 89:121–146, (1976). Synthases from various plant species that produce a number of Golgi-synthesized polysaccharides have been detected and partially characterized. Bolwell, G. P. *Phyto chemistry* 27:1235–1253 (1998). In the past, progress toward identification and purification of the polypeptides responsible for these synthase activities has been rather slow. This is mainly because all these enzymes are membrane-associated and are rather labile (Bolwell, supra).

The present invention, however, elucidates one or more polypeptides involved in the synthesis of cell wall polysaccharides. Glycosylation of the polypeptides is reversible. Thus, these polypeptides are termed reversibly glycolsylated polypeptides (RGP). In particular, it is believed that these RGPs are involved in glucan synthase-1 (GS-1) activity.

GS-1 is one of a variety of membrane bound synthases that use sugar nucleotides as glycosyl donors for forming cell wall polysaccharides. Hassid, *Biochemistry of the Glycosidic Linkage,* Piras et al., Eds., Academic Press, N.Y. pp. 315–335 (1972). It is present in the Golgi system, not at the plasma membrane. Thus, it is believed that the function of GS-I is to form the (1,4)-β-glucan backbone of xyloglucan, an important hemicellulosic polysaccharide synthesized in the Golgi system. Dhugga, et al., "Plant Polypeptides Reversibly Glycosylated by UDP-Glucose" *J. of Biological Chemistry* 266:21977–21984 (1991). Thus, the RGPs disclosed herein have an important function in the formation of hemicellulose.

In monocot cell walls, the major hemicellulose polysaccharide is arabinoxylan; xyloglucan is present but at a very low concentration. It is believed that arabinoxylan performs the same function in monocots as xyloglucan in dicots.

Reducing arabinoxylan concentration will lead to an increase in cellulose content in the cell wall. Reducing the concentration of arabinoxylan in the grain will improve starch extractability.

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as: increasing starch extractibility for the wet-milling process, improving the soluble fiber content of grain for human consumption, improving the feed converison ratio of grain for livestock feed, and improving grain handling quality. The present invention also provides utility in altering the arabinoxylan or xyloglucan level of plants to affect growth rate and stalk or stem quality.

The present invention also provides isolated nucleic acids comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including Hordeum, Secale, Triticum, Sorghum (e.g., *S. bicolor*) and Zea (e.g., *Z. mays*). The isolated nucleic acid and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Glycine, Pisum, Phaseolus, Lolium, Oryza, and Avena.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of SEQ ID NOS: 2 and 4 and conservatively modified and polymorphic variants thereof, including exemplary polynucleotides of SEQ ID NOS: 1 and 3;

(b) a polynucleotide which is the product of amplification from a *Zea mays* nucleic acid library using primer pairs which selectively hybridize under stringent conditions to loci within a polynucleotide selected from the group consisting of SEQ ID NOS: 5 and 6, or 7 and 8;

(c) a polynucleotide which selectively hybridizes to a polynucleotide of (a) or (b);

(d) a polynucleotide having a specified sequence identity with polynucleotides of (a), (b), or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d), or (e); and (g) a polynucleotide comprising at least a specific number of contiguous nucleotides from a polynucleotide of (a), (b), (c), (d), (e), or (f).

A. Polynucleotides Encoding A Polypeptide of the Present Invention or Conservatively Modified or Polymorphic Variants Thereof As indicated in (a), above, the present invention provides isolated nucleic acids comprising a polynucleotide of the present invention, wherein the polynucleotide encodes a polypeptide of the present invention, or conservatively modified or polymorphic variants thereof. Accordingly, the present invention includes polynucleotides of SEQ ID NOS: 1 and 3, and silent variations of polynucleotides encoding a polypeptide of SEQ ID NOS: 2 and 4. The present invention further provides isolated nucleic acids comprising polynucleotides encoding conservatively modified variants of a polypeptide of SEQ ID NOS: 2 and 4. Conservatively modified variants can be used to generate or select antibodies immunoreactive to the non-variant polypeptide. Additionally, the present invention further provides isolated nucleic acids comprising polynucleotides encoding one or more allelic (polymorphic) variants of polypeptides/polynucleotides. Polymorphic variants are frequently used to follow segregation of chromosomal regions in, for example, marker assisted selection methods for crop improvement.

B. Polynucleotides Amplified from a Zea mays Nucleic Acid Library

As indicated in (b), above, the present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, S. *Gene* 138: 171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371, 1995). cDNA synthesis is often catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly growing tissues, or rapidly dividing cells are preferably used as mRNA sources.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a “tail”) can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog 97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology,* Unit 15.6, Ausubel, et al., Eds., Greene Publishing and Wiley-Interscience, New York (1995); Frohman and Martin, *Techniques* 1:165 (1989).

C. Polynucleotides Which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cofton, wheat, sorghum, sunflower, alfalfa, oats, sugar cane, millet, barley, and rice. Optionally, the CDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B), or (C), above. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See PCT Patent publication Nos. 92/05258, 92/14843, and 97/20078. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), above, the present invention provides isolated nucleic acids comprising polynucleotides complementary to the polynucleotides of paragraphs A–E, above. As those of skill in the art will recognize, complementary sequences base-pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is *Zea mays*.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A 1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of organelles and proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual,* Clark, Ed., Springer-Verlag, Berlin (1997); and, *Current Protocols in Molecular Biology, Ausubel,* et al., Eds., Greene Publishing and Wiley-lnterscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'–3' (Paoli Inc., Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a CDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded CDNA, typically by reaction with a combination of RNAse H and DNA polymerase I (or Klenow fragment). Third, the termini of the double stranded CDNA are ligated to adaptors. Ligation of the adaptors can produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. CDNA synthesis protocols are well known to the skilled artisan and are described in such standard references as: *Plant Molecular Biology: A Laboratory Manual,* Clark, Ed., Springer-Verlag, Berlin (1997); and, *Current Protocols in Molecular Biology,* Ausubel, et al., Eds., Greene Publishing and Wiley-lnterscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., *Genomics,* 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.,* 15(6):3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.,* 18(19):5705–5711 (1990); Patanjali et al., *Proc. Natl. Acad. U.S.A.,* 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci.* USA, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining unhybridized cDNA pool is enriched for sequences unique to that pool. See, Foote et al. in, *Plant Molecular Biology: A Laboratory Manual,* Clark, Ed., Springer-Verlag, Berlin (1997); Kho and Zarbl, *Technique,* 3(2):58–63 (1991); Sive and St. John, *Nucl. Acids Res.,* 16(22):10937 (1988); *Current Protocols in Molecular Biology, Ausubel,* et al., Eds., Greene Publishing and Wiley-lnterscience, New York (1995); and, Swaroop et al., *Nucl. Acids Res.,* 19(8):1954 (1991). CDNA subtraction kits are commercially available. See, e.g., PCR-Select (Clontech, Palo Alto, Calif.).

A4. Construction of a Genomic Library

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual,* 2nd Ed., Cold Spring Harbor Laboratory Vols. 1–3 (1989), Methods in Enzymology, Vol. 152, *Guide to Molecular Cloning Techniques,* Berger and Kimmel, Eds., San Diego: Academic Press, Inc. (1987), *Current Protocols in Molecular Biology,* Ausubel, et al., Eds., Greene Publishing and Wiley-lnterscience, New York (1995); *Plant Molecular Biology: A Laboratory Manual,* Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications,* Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.,* 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Casseftes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumefaciens,* the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays,* operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook,* Chapters 114–115, Freeling and Walbot, Eds., Springer, New York (1994); *Corn and Corn Improvement,* 3rd edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that does not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook,* Chapter 114, Freeling and Walbot, Eds., Springer, New York, (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants,* Kosage, Meredith and Hollaender, Eds., pp. 221–227, 1983. In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook,* Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci.* (USA) 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2:279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc (*1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

The present invention further provides a protein comprising a polypeptide having a specified sequence identity with a polypeptide of the present invention. The percentage of sequence identity is an integer selected from the group consisting of from 60 to 99. Exemplary sequence identity values include 60%, 65%, 70%, 75%, 80%, 85%, 90%, and 95%.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli;* however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., *Gene* 22:229–235 (1983); Mosbach, et al., *Nature* 302:543–545 (1983)).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics,* Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris.* Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89:49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, *J. Embryol. Exp. Morphol.* 27:353–365 (1987).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach,* D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

A DNA sequence coding for the desired polypeptide of the present invention, for example a cDNA or a genomic sequence encoding a full length protein, will be used to construct a recombinant expression cassette which can be introduced into the desired plant.

Isolated nucleic acid acids of the present invention can be introduced into plants according to techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising et al., *Ann. Rev. Genet.* 22:421–477 (1988). For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp.197–213 in Plant Cell, Tissue and Organ Culture, Fundamental Methods. eds. O. L. Gamborg and G. C. Phillips. Springer-Verlag, Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using PEG precipitation is described in Paszkowski et al., *Embo J.* 3: 2717–2722 (1984). Electroporation techniques are described in Fromm et al., *Proc. Natl. Acad. Sci.* (USA) 82: 5824 (1985). Ballistic transformation techniques are described in Klein et al., *Nature* 327:70–73 (1987). *Agrobacterium tumefaciens*-mediated transformation techniques are well described in the scientific literature. See, for example Horsch et al., *Science* 233: 496–498 (1984), and Fraley et al., *Proc. Natl. Acad. Sci.* (USA) 80:4803 (1983). Although Agrobacterium is useful primarily in dicots, certain monocots can be transformed by Agrobacterium. For instance, Agrobacterium transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of A. rhizogenes strain A4 and its Ri plasmid along with *A. tumefaciens* vectors pARC8 or pARC16 (2) liposome-mediated DNA uptake (see, e.g., Freeman et al., *Plant Cell Physiol.* 25: 353 (1984)), (3) the vortexing method (see, e.g., Kindle, *Proc. Natl. Acad. Sci.,* (USA) 87:1228 (1990).

DNA can also be introduced into plants by direct DNA transfer into pollen as described by Zhou et al., Methods in Enzymology, 101:433 (1983); D. Hess, *Intern Rev. Cytol.,* 107:367 (1987); Luo et al., *Plant Mol. Biol. Reporter,* 6:165 (1988). Expression of polypeptide coding genes can be obtained by injection of the DNA into reproductive organs of a plant as described by Pena et al., *Nature,* 325:274 (1987). DNA can also be injected directly into the cells of immature embryos and the rehydration of desiccated embryos as described by Neuhaus et al., *Theor. Appl. Genet.,* 75:30 (1987); and Benbrook et al., in *Proceedings Bio Expo* 1986, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology,* Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence.

Techniques for solid phase synthesis are described by Barany and Merrifield, Solid-Phase Peptide Synthesis, pp. 3–284 in *The Peptides: Analysis, Synthesis, Biology.* Vol. 2: *Special Methods in Peptide Synthesis, Part A.;* Merrifield, etal., *J. Am. Chem. Soc.* 85:2149–2156 (1963), and *Stewart et al., Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice,* Springer-Verlag: New York (1982); Deutscher, *Guide to Protein Purification,* Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phyto-hormones in a tissue culture growth medium. For transformation and regeneration of maize see, Gordon-Kamm et al., *The Plant Cell,* 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillan Publishing Company, New York, pp. 124–176 (1983); and Binding, *Regeneration of Plants, Plant Protoplasts,* CRC Press, Boca Raton, pp. 21–73 (1985).

The regeneration of plants containing the foreign gene introduced by Agrobacterium from leaf explants can be achieved as described by Horsch et al., *Science,* 227:1229–1231 (1985). In this procedure, transformants are grown in the presence of a selection agent and in a medium that induces the regeneration of shoots in the plant species being transformed as described by Fraley et al., *Proc. Natl. Acad. Sci.* (U.S.A.), 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook,* Freeling and Walbot, Eds., Springer, New York (1994); *Corn and Corn Improvement,* 3rd edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non- transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the the ratio of the polypeptides of the present invention in a plant. The method comprises introducing into a plant cell a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance.

See, e.g., Clark, Ed., *Plant Molecular Biology: A Laboratory Manual.* Berlin, Springer-Verlag, 1997. Chapter 7. For molecular marker methods, see generally, "The DNA Revolution" in: Paterson, A. H., *Genome Mapping in Plants* (Austin, Tex., Academic Press/R. G. Landis Company, 1996) pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.*15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12:387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.-H., et al. *Proc. Natl. Acad. Sci.* USA 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology,* F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, MD) ALIGNX, or Genecode's (Ann Arbor, Mich.) SEQUENCHER. Conveniently, default parameters of such software can be used to generate consensus or generic sequences.

Computer Applications

The present invention provides machines, data structures, and processes for modeling or analyzing the polynucleotides and polypeptides of the present invention.

A. Machines and Data Structures

The present invention provides a machine having a memory comprising data representing a sequence of a polynucleotide or polypeptide of the present invention. The machine of the present invention is typically a digital computer. The memory of such a machine includes, but is not limited to, ROM, or RAM, or computer readable media such as, but not limited to, magnetic media such as computer disks or hard drives, or media such as CD-ROM. Thus, the present invention also provides a data structure comprising a sequence of a polynucleotide of the present invention embodied in a computer readable medium. As those of skill in the art will be aware, the form of memory of a machine of the present invention or the particular embodiment of the computer readable medium is not a critical element of the invention and can take a variety of forms.

B. Homology Searches

The present invention provides a process for identifying a candidate homologue (i.e., an ortholog or paralog) of a polynucleotide or polypeptide of the present invention. A candidate homologue has statistically significant probability of having the same biological function (e.g., catalyzes the same reaction, binds to homologous proteins/nucleic acids) as the reference sequence to which it's compared. Accordingly, the polynucleotides and polypeptides of the present invention have utility in identifying homologs in animals or other plant species, particularly those in the family Gramineae such as, but not limited to, sorghum, wheat, or rice.

The process of the present invention comprises obtaining data representing a polynucleotide or polypeptide test sequence. Test sequences are generally at least 25 amino acids in length or at least 50 nucleotides in length. Optionally, the test sequence can be at least 50, 100, 150, 200, 250, 300, or 400 amino acids in length. A test polynucleotide can be at least 50, 100, 200, 300, 400, or 500 nucleotides in length. Often the test sequence will be a full-length sequence. Test sequences can be obtained from a nucleic acid of an animal or plant. Optionally, the test sequence is obtained from a plant species other than maize whose function is uncertain but will be compared to the test sequence to determine sequence similarity or sequence identity; for example, such plant species can be of the family Gramineae, such as wheat, rice, or sorghum. The test sequence data are entered into a machine, typically a computer, having a memory that contains data representing a reference sequence. The reference sequence can be the sequence of a polypeptide or a polynucleotide of the present invention and is often at least 25 amino acids or 100 nucleotides in length. As those of skill in the art are aware, the greater the sequence identity/similarity between a reference sequence of known function and a test sequence, the greater the probability that the test sequence will have the same or similar function as the reference sequence.

The machine further comprises a sequence comparison means for determining the sequence identity or similarity between the test sequence and the reference sequence. Exemplary sequence comparison means are provided for in sequence analysis software discussed previously. Optionally, sequence comparison is established using the BLAST suite of programs.

The results of the comparison between the test and reference sequences can be displayed. Generally, a smallest sum probability value (P(N)) of less than 0.1, or alternatively, less than 0.01, 0.001, 0.0001, or 0.00001 using the BLAST 2.0 suite of algorithms under default parameters identifies the test sequence as a candidate homologue (i.e., an allele, ortholog, or paralog) of the reference sequence. A nucleic acid comprising a polynucleotide having the sequence of the candidate homologue can be constructed using well known library isolation, cloning, or in vitro synthetic chemistry techniques (e.g., phosphoramidite) such as those described herein. In additional embodiments, a nucleic acid comprising a polynucleotide having a sequence represented by the candidate homologue is introduced into a plant; typically, these polynucleotides are operably linked to a promoter. Confirmation of the function of the candidate homologue can be established by operably linking the candidate homolog nucleic acid to, for example, an inducible promoter, or by expressing the antisense transcript, and analyzing the plant for changes in phenotype consistent with the presumed function of the candidate homolog. Optionally, the plant into which these nucleic acids are introduced is a monocot such as from the family Gramineae. Exemplary plants include maize, sorghum, wheat, rice, canola, alfalfa, cotton, and soybean.

C. Computer Modeling

The present invention provides a process of modeling/analyzing data representative of the sequence a polynucleotide or polypeptide of the present invention. The process comprises entering sequence data of a polynucleotide or polypeptide of the present invention into a machine, manipulating the data to model or analyze the structure or activity of the polynucleotide or polypeptide, and displaying the results of the modeling or analysis. A variety of modeling and analytic tools are well known in the art and available from such commercial vendors as Genetics Computer Group (Version 9, Madison, Wis.). Included amongst the modeling/analysis tools are methods to: 1) recognize overlapping sequences (e.g., from a sequencing project) with a polynucleotide of the present invention and create an alignment called a "contig"; 2) identify restriction enzyme sites of a polynucleotide of the present invention; 3) identify the products of a T1 ribonuclease digestion of a polynucleotide of the present invention; 4) identify PCR primers with minimal self-complementarity; 5) compare two protein or nucleic acid sequences and identifying points of similarity or dissimilarity between them; 6) compute pairwise distances between sequences in an alignment, reconstruct phylogentic trees using distance methods, and calculate the degree of divergence of two protein coding regions; 7) identify patterns such as coding regions, terminators, repeats, and other consensus patterns in polynucleotides of the present invention; 8) identify RNA secondary structure; 9) identify sequence motifs, isoelectric point, secondary structure, hydrophobicity, and antigenicity in polypeptides of the present invention; and, 10) translate polynucleotides of the present invention and backtranslate polypeptides of the present invention.

Detection of Nucleic Acids

The present invention further provides methods for detecting a polynucleotide of the present invention in a nucleic acid sample suspected of containing a polynucleotide of the present invention, such as a plant cell lysate, particularly a lysate of maize. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3):230–250 (1986); Haase et al., *Methods in Virology,* Vol. VII, pp.189–226 (1984); Wilkinson, The theory and practice of in situ hybridization in: *In situ Hybridization,* D. G. Wilkinson, Ed., IRL Press, Oxford University Press, Oxford; and *Nucleic Acid Hybridization: A Practical Approach,* Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radioactive isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase. Means of detecting such labels are well known to those of skill in the art. Thus, for example, radiolabels may be detected using photographic film or scintillation counters, fluorescent markers may be Detected using aphotodetector to detect emitted light. Enzymatic labels are typically detected by providing the enzyme with a substrate and detecting the reaction product produced by the action of the enzyme on the substrate, and calorimetric labels are detected by simply visualizing the colored label.

Antibodies to Proteins

Antibodies can be raised to a protein of the present invention including individual, allelic, strain, or species variants, and fragments thereof, both in their naturally occurring (full-length) forms and in recombinant forms. Additionally, antibodies are raised to these proteins in either their native configurations or in non-native configurations. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., J. Janin, *Nature,* 277 (1979) 491–492; Wolfenden, et al., *Biochemistry* 20 (1981) 849–855; Kyte and Doolite, *J. Mol Biol.* 157 (1982) 105–132; Rose, et al., *Science* 229 (1985) 834–838. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native polynucleotide of the present invention are the preferred antigens for the production of monoclonal or polyclonal antibodies. Polypeptides of the present invention are optionally denatured, and optionally reduced, prior to formation of antibodies for screening expression libraries or other assays in which a putative protein of the present invention is expressed or denatured in a non-native secondary, tertiary, or quartenary structure.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an antigen, preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology,* Wiley/Greene, N.Y. (1991); and Harlow and Lane, *Antibodies: A Laboratory Manual,* Cold Spring Harbor Press, N.Y. (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from hyrbrid cells secreting the desired antibody. Monoclonals antibodies are screened for binding to a protein from which the antigen was derived. Specific monoclonal and polyclonal antibodies will usually have an antibody binding site with an affinity constant for its cognate monovalent antigen at least between $10^{6}$–$10^{7}$, usually at least $10^{8}$, preferably at least $10^{9}$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology,* 4th ed., Stites et al., Eds., Lange Medical Publications, Los Altos, Calif., and references cited therein; Harlow and Lane, Supra; Goding, *Monoclonal Antibodies: Principles and Practice,* 2nd ed., Academic Press, New York, N.Y. (1986); and Kohler and Milstein, *Nature* 256:495–497 (1975). Summarized briefly, this method proceeds by injecting an animal with an antigen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the antigen. In this manner, the individual antibody species obtained are the products of immortalized and cloned single B cells from the immune animal generated in response to a specific site recognized on the antigenic substance.

Other suitable techniques involve selection of libraries of recombinant antibodies in phage or similar vectors (see, e.g., Huse et al., *Science* 246:1275–1281 (1989); and Ward, et al., *Nature* 341:544–546 (1989); and Vaughan et al., *Nature Biotechnology,* 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.,* 14:845–851 (1996). Also, recombinant immunoglobulins may be produced. See, Cabilly, U.S. Pat. No. 4,816,567; and Queen et al., *Proc. Nat'l Acad. Sci.* 86: 0029–10033 (1989).

The antibodies of this invention are also used for affinity chromatography in isolating proteins of the present invention. Columns are prepared, e.g., with the antibodies linked to a solid support, e.g., particles, such as agarose, SEPHADEX, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding.

Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Protein Immunoassays

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology,* Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay,* Maggio, Ed., CRC Press, Boca Raton, Fla. (1980); Tijan, Practice and Theory of Enzyme Immunoassays, *Laboratory Techniques in Biochemistry and Molecular Biology,* Elsevier Science Publishers B. V., Amsterdam (1985); Harlow and Lane, supra; *Immunoassay: A Practical Guide,* Chan, Ed., Academic Press, Orlando, Fla. (1987); *Principles and Practice of Immunoassaysm,* Price and Newman Eds., Stockton Press, N.Y. (1991); and *Non-isotopic Immunoassays,* Ngo, Ed., Plenum Press, N.Y. (1988). Immunological binding assays (or immunoassays) typically utilize a "capture agent" to specifically bind to and often immobilize the analyte (in this case, a protein of the present invention). The capture agent is a moiety that specifically binds to the analyte. In a preferred embodiment, the capture agent is an antibody that specifically binds a protein(s) of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (See, generally Kronval, et al., *J. Immunol.* 111:1401–1406 (1973), and Akerstrom, et al., *J. Immunol.* 135:2589–2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A. Non-Competitive Assay Formats

Immunoassays for detecting proteins of the present invention include competitive and noncompetitive formats. Noncompetitive immunoassays are assays in which the amount of captured analyte (i.e., a protein of the present invention) is directly measured. In one preferred "sandwich" assay, for example, the capture agent (e.g., an antibody specifically reactive, under immunoreactive conditions, to a protein of the present invention) can be bound directly to a solid substrate where they are immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In a particularly preferred embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another preferred competitive assay. In this assay a known analyte, (such as a protein of the present invention) is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Generation of pooled antisera for use in immunoassays

A protein that specifically binds to or that is specifically immunoreactive with an antibody generated against a defined antigen is determined in an immunoassay. The immunoassay uses a polyclonal antiserum which is raised to a polypeptide of the present invention (i.e., the antigenic polypeptide). This antiserum is selected to have low crossreactivity against other proteins and any such crossreactivity is removed by immunoabsorbtion prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide of the present invention is isolated as described herein. For example, recombinant protein can be produced in a mammalian or other eukaryotic cell line. An inbred strain of mice is immunized with the protein using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, supra, at pages 570–573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for crossreactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent crossreactivity for the above proteins is calculated, using standard calculations. Those antisera with less than 10% crossreactivity with a distinct form of a polypeptide are selected and pooled. The cross-reacting antibodies are then removed from the pooled antisera by immunoabsorbtion with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In a particularly preferred embodiment, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a protein of the present invention. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

E. Quantification of Proteins.

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

G. Immunoassay Labels

The labeling agent can be, e.g., a monoclonal antibody, a polyclonal antibody, a binding protein or complex, or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes, radiolabels, enzymes, and calorimetric labels or colored glass or plastic beads, as discussed for nucleic acid labels, supra.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDS) or photomultipliers and the like. Similarly, enzymatic labels may be detected by providing appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Generally, the polypeptide will be present in a range sufficient to determine the effect of the compound, typically about 1 nM to 10 $\mu$M. Likewise, the compound will be present in a concentration of from about 1 nM to 10 $\mu$M. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations,* 2$^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

EXAMPLE 1

Construction of the CDNA libraries

Total RNA Isolation

Total RNA was isolated from maize tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringency conditions and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first strand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P—dCTP and a portion of the reaction was analyzed by agarose gel electrophoresis to determine CDNA sizes. CDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2 cDNA sequencing and library subtraction

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 cm$^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, $2^{nd}$ Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire maize sequence database.
4. A Sal-A20 oligo nucleotide: TCG ACC CAC GCG TCC GAA AAA AAA AAA AAA AAA AAA, removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

Identification of the gene from a computer homology search

Gene identities were determined by conducting BLAST (Basic Local Alignment Search Tool; Altschul, S. F., et al., (1993) *J. Mol Biol.* 215:403–410; see also www.ncbi.nim.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA were used to construct contiguous DNA sequences.

EXAMPLE 4

Purification of maize RGP

All the following operations were performed on ice and/or 4° C. Developing kernels from 27–28 days after pollination (DAP) maize ears were harvested and 360 g kernels were homogenized in 800 ml Mops homogenization medium or MHM (100 mM Mops, pH 7.0, 0.25 M sucrose, 1 mM EDTA, 10 mM KCl) in a blender. After squeezing through four layers of cheesecloth, the filtrate was centrifuged first at 1000×g for 10 min to remove cell wall debris and then at 125,000×g for 1 hr to pellet the membrane fraction. The pellet was re-suspended in 10 ml MHM. Approximately 15 mg protein per gram of kernels was recovered of which 25% was in the pellet and the rest in the soluble fraction. To the supernatant was added $MnCl_2$ to a final concentration of 15 mM. The mixture stirred gently for 6 hours and then centrifuged at 15,000×g for 30 min. The pellet was discarded and to the supernatant 10 mM more $MnCl_2$ was added and the solution was stirred for 16 hours. The solution was centrifuged at 125,000×g for 1 hour, pellet discarded and supernatant saved. After adding 5 mM more $MnCl_2$, the supernatant was passed through a UDP-glucuronate-agarose column and the protein was purified as described (Dhugga et al, 1998, PNAS, 94, 7679–7684).

EXAMPLE 5

Expression of RGP in developing kernels

A) Proteins

Kernels or kernel parts from various stages of development were homogenized as described in the previous section and centrifuged at 1000×g for 10 min. From one stage, 27-DAP, the kernels was dissected into embryo, endosperm, and pericarp and the isolated parts homogenized as above. Equal amounts of protein from kernels of various ages as well as kernel parts were subjected to SDS/PAGE. After transferring proteins to a nitrocellulose sheet, the blot was subjected to Western blotting as described previously using anti-PsRGP1 antibody (Dhugga et al, 1998, *PNAS,* 94, 7679–7684). RGP was most abundant early in development, i.e., at 10-DAP. Consequent with a reduction in its expression as the kernel development progressed, small molecular mass fragments resulting apparently from RGP breakdown were observed at 27-DAP the intensity of which increased by 45-DAP. Among the 27-DAP kernel parts, RGP was most highly expressed in the pericarp and least expressed in the endosperm. Expression in the embryo was close to that of pericarp. This expression profile is very similar to the concentration of cell wall in these parts as a proportion of cell dry mass, supporting the role of RGP in cell wall synthesis.

By immunocytochemical localization using pea anti-RPG antibody, RGP is primarily found in the young, dividing and expanding cells in the developing maize kernels. The expression pattern generally matches that obtained from the Western blot analysis. The young cells that are expanding and therefore synthesizing new cell wall have remarkably higher concentration of RGP than the fully expanded ones. The cells in the placental region, peripheral layers of the developing endosperm, and embryo are particularly rich in RGP protein. The concentration of RGP is even lower in the endosperm than detected by Western blotting as a majority of the RGP seemed to have been derived from the residual surface layers (later to become aleurone) surrounding the endosperm. The observation that the RGP concentration is related either to the rate of wall synthesis or the concentration of the cell wall in certain cell types supports the role of RGP in cell wall synthesis.

B) mRNA

Twenty micrograms of total RNA were run in duplicate on a 1% urea/formaldehyde gel then blotted onto a Zetaprobe™ GT Genomic nylon membrane using the standard neutral transfer protocol described in the Schleicher & Schuell 3/696 pamphlet. CCMCA47-1 DNA was digested with ApoI and the 1.0 kb internal Rgp2 fragment was gel-purified using the Qiagen Qiaquick™ Gel Extraction kit. One ng of purified fragment was subjected to PCR-mediated DIG-labeling using Rgp2-specific forward and reverse primers. Protocol was as described in the Boehringer Mannheim PCR DIG Probe Synthesis™ kit. The 736bp EcoRV/ApoI internal DNA fragment from the Rgp1 (CGEUH36) *E. coli* expression clone, CX36, was similarly purified and labeled using Rgp1-specific forward and reverse primers. PCR reactions were run on a 1% TAE gel and the DIG-labeled PCR products were gel-purified as above.

The Northern blots were prehybridized at 42° C. for five hours in a freshly prepared Hybridization solution (50% formamide, 0.02% SDS, 0.1% N-lauryl sarcosine, and 2% Blocking reagentTM [Boehringer Mannheim]). Rgp1 and Rgp2 DIG-labeled fragments were boiled at 100° C., 10 minutes, briefly kept in ice and then added to prewarmed (42° C.) Hybridization solution to final concentrations of 20 ng/ml and 10 ng/ml respectively. These probe solutions were added to the blots and hybridization was allowed to proceed at 42° C. overnight.

Blots were washed twice at room temperature for 15 min each in 2X SSC, 0.1% SDS and three times at 65° C. for 30 min each in 0.5X SSC, 0.1% SDS. DIG Chemiluminescent Detection (Boehringer Mannheim DIG Detection kit) was used to detect the hybridized probe. Blots were washed in maleate buffer+0.3% Tween-20, 5 min at room temperature and then soaked in blocking solution for 1 hour at room temperature. Antibody solution (1:5000 dilution of anti-DIG alkaline phosphatase-coupled antibody in blocking solution) was added to drained blots in roller bottles and incubation allowed to proceed for 40 min at room temperature. Blots were washed twice for 1 hour each in wash buffer and then equilibrated for 5 min in detection buffer. CSPD was added to drained blots for 5 min at room temperature and then drained. Blots were placed on Kodak™ X-OMAT AR film for 10, 20, 40 and 60 min exposure time and developed in an X-ray film developing machine.

Northern blot analyses indicated that both Rgp1 and Rgp2 are expressed in every tissue tested, i.e., kernel, root, leaf. Rgp1 is highly expressed in the pericarp and young leaf tissue and its mRNA abundance is comparatively low in the endosperm and embryo. Overall, the Northern results mirror the Western results. Rgp2, however, appears to be preferentially expressed in the embryo where its abundance is greater than that in the pericarp or other plant tissues. It appears that Rgp2 is embryo-preferred. This may have been the reason for the lack of Rgp2 ESTs in non-embryo tissue libraries.

EXAMPLE 6

Determination of effects of Mutator (Mu) insertions into Rgp1 and Rgp2 genes

This example describes the procedure to identify plants containing Mu inserted into either Rgp1 or Rgp2 gene, and strategy to identify the function of these genes.

The Trait Utility System for Corn (TUSC) is a method that employs genetic and molecular techniques to facilitate the study of gene function in maize. Studying gene function implies that the gene's sequence is already known, thus the method works in reverse: from sequence to phenotype. This kind of application is referred to as "reverse genetics", which contrasts with "forward" methods (such as transposon tagging) that are designed to identify and isolate the gene(s) responsible for a particular trait (phenotype).

Pioneer Hi-Bred International, Inc., has its proprietary collection of maize genomic DNA from approximately 42,000 individual F1 plants (Reverse genetics for maize, Meeley, R and Briggs, S, 1995, *Maize Genet. Coop. Newslett.* 69:67,82). The genome of each of these individuals contains multiple copies of the transposable element family, Mutator (Mu). The Mu family is highly mutagenic; in the presence of the active element Mu—DR, these elements transpose throughout the genome, inserting into genic regions, and often disrupting gene function. By collecting genomic DNA from a large number of individuals (42,000), Pioneer has assembled a library of the mutagenized maize genome. Mu insertion events are predominately heterozygous so, given the recessive nature of most insertional mutations, the F1 plants appear wild-type. Each of the plants was selfed to produce F2 seed, which was collected. In generating the F2 progeny, insertional mutations segregate in a Mendelian fashion so are useful for investigating a mutant allele's effect on the phenotype. The TUSC system has been successfully used by a number of laboratories to identify the function of a variety of genes (Cloning and characterization of the maize An1 gene, Bensen, R J et al., 1995, *Plant Cell* 7:75–84; Diversification of C-function activity in maize flower development, Mena, M et al., 1996, *Science* 274:1537–1540; Analysis of a chemical plant defense mechanism in grasses, Frey, M. et al., 1997, *Science* 277:696–699. The control of maize spikelet meristem fate by the APETALA2-like gene Indeterminate spikelet 1, Chuck, G, Meeley, R B, and Hake, S, 1998, *Genes & Development* 12:1145–1154; A SecY homologue is required for the elaboration of the chloroplast thylakoid membrane and for normal chloroplast gene expression, Roy, L M and Barkan, A., 1998, *J. Cell Biol.* 141:1–11).

PCR Screening for Mu insertions in Rgp1

Two primers were designed from within the Rgp1 cDNA, identified in FIG. 5 as Gene-Specific Primer (GSP) 1 (forward) and 2 (reverse):

Forward primer: 5'- TCT TGA GCA GCA CAT CAA GAA CCT CCT C-3' (position 477–504, Table 2)

Reverse primer: 5'- TGC CGA AGT GAT GGC ACA TCT ACT TGG-3' (complementary to position 1213–1187, Table 2)

Mu TIR primer: 5'- AGA GAA GCC AAC GCC AWC GCC TCY ATT TCG TC-3'

To select primers for PCR we used Pickoligo. This program chooses the $T_m$ according to the following equation:

$$T_m=[((GC*3+AT*2)*37-562)/length]-5$$

The primers we designed had~68° C. $T_m$.

PCR reactions were run with an annealing temperature of 62° C. and a thermocycling profile as follows: initial denaturation: 94° C. for 2 minutes; 35 cycles of: 94° C. for 30 sec. to 1 min.; 62° C. for 30 sec. to 1 min.; 72° C. for 1 to 3 minutes; and a final denaturation step of 72° C. for 5 minutes.

That there was no false priming in single primer reactions and only one fragment was amplified in paired GSP reactions, was confirmed by DNA gel-blots using Rgp1 cDNA as a hybridization probe.

The genomic DNA from 42,000 plants, combined into pools of 48 plants each, was subjected to PCR with either GSP1 or GSP2 and Mu TIR. The pools that were confirmed to be positive by dot-blot hybridization using Rgp1 cDNA as a probe were subjected to gel-blot analysis in order to determine the size of fragments amplified. The pools in which clean fragments were identified were subjected to further analysis to identify the individual plants within those pools that contained Mu insertion(s).

Seed from F1 plants identified in this manner was planted in the field in the summer of 1997. Leaf discs from twenty plants from each F2 row were collected and genomic DNA isolated. The same twenty plants were selfed and the F3 seed saved. Pooled DNA (from 20 plants) from each of the twelve rows was subjected to PCR using GSP1 or GSP2 and Mu TIR primer as mentioned above. Two pools identified to contain Mu insertions were subjected to individual plant analysis and homozygotes identified. In one case the Mu appeared to be inserted at position 582 and in the second case at position 727 of the Rgp1 cDNA. The seed from these two individual plants has been planted in the field. The tissue samples will be analyzed for carbohydrate composition.

TUSC for Rgp2 gene

The following primers along with the Mu TIR primer (same as used for Rgp1) were used to identify twelve different individual F1 plants that apparently contained Mu in the genic region of Rgp2.

Forward primer 5'-CAG ACA TGG CAG AGG ATC TTC AAA TCC CT- 3'

Reverse primer 5'-TGC AGT CCT CGA TAG CTT GAG CGA CT-3'

These plants are planted in the field and are subjected to similar analyses as for Rgp1. Our goal is to combine the mutated Rgp1 and Rgp2 genes into a single individual to see if they lead to reduced arabinoxylan accumulation in the cell walls.

EXAMPLE 7

Purification and analysis of pea RGP1

Peas, Pisum sativum L. cv., early Alaska, were grown for 8 days under dim red light. Dhugga, K.S. et al., *J. BioL.Chem.* 266: 21977–21984 (1991). Tissue from the 2 cm of stem just below the apical hook was homogenized and centrifuged as described in Dhugga, K.S. et al., *J. Biol. Chem.* 266:21977–21984 (1991), except that the post-1000×g supernatant was centrifuged at 120,000×g. The supernatant was brought to 40% saturation with $(NH_4)_2SO_4$ and, after 2 hr in ice, was centrifuged 20 min. at 30,000×g. The pellet was resuspended in 50 mM Mops (pH 7.0) and dialyzed against this buffer overnight. 15 mM $MnCl_2$ was added, and after approximately 12 hr in ice, the mixture was centrifuged 20 min at 30,000×g. The supernatant was passed through 5 ml of UDP-glucuronic and agarose (Sigma) equilibrated with resuspension buffer containing 5 mM $MnCl_2$. The column was washed with this buffer until the $A_{280}$ of the effluent approached zero. RGP1 was eluted with resuspension buffer containing 1 mM EDTA and no $Mn^{2+}$.

Glycosylation Assay

RGP1 was incubated normally for 5 min. at 22° C. with UDP-[14C]Glc or another labled UDP sugar in 50 mM Mops buffer (pH7.0) containing 5 mM MnCl2 terminated by adding 80% ethanol, and collecting insoluble material on a glass fiber paper disc, as described for GS-I assay in Ray, P. M., Plant Physiol. 78:466–472 (1985). This assay is satisfactory for glycosylation of purified RGP1 because (in contrast to membrane preparations) with RGP1 alone no polysaccharide is formed from UDP-Glc or other donors.

Peptide Sequencing

RGP1 protein was precipitated with 9 vol. of 9:1 (vol/vol) methanol:chloroform, re-susupended in 2 Murea/100 mM NH4HCO3. To 20 μg of protein, 1 μg of trypsin (Boehringer Mannheim) suspended in 0.01% (wt./vol.) trifluoroacetic acid (TFA) was added and kept overnight at 37° C., 2.5%. TFA was added and, after centrifugation, the supernatant was fractionated by HPLC on a C-4 column (250 mm×5 μm; Vyda, Hesperia, Calif.) with a gradient of 3.5–70% (vol/vol) acetonitrile in water with 0.1% TFA in the water and 0.025% TFA in the acetonitrile solution. A212 was recorded on-line and peaks were collected manually. Material from two clean-looking peaks were pooled and rechromatographed: the resulting peaks were sequenced by the Stanford Protein and Nucleic Acids Facility.

Antiserum

RGP1 purified as described above was further purified by SDS/PAGE and electroelution and antiserum was raised as described for other proeins in Dhugga, K. S. and Ray, P. M. Eur. J. Biochem. 220:943–953 (1994), except that twice as much RGP1 was used for each injection. After the first bleeding following the third injection, booster shots of 50–100 μg RGP1 in incomplete adjuvant were given at approximately 10-week intervals, between which the rabbit was bled twice.

Anti-RGP1 antibodies were isolated from antiserum by adsorption to RGP1 protein expressed in Escherichia coli from cloned Rgp1 cDNA, using the method of Johnson et al., Cell 43:369–377 (1985).

Electrophoresis and Blotting

SDS/PAGE was performed as described in Dhugga et al., J. Biol. Chem. 266:21977–21984 (1991) and the separated proteins were blotted onto nitrocellulose sheets. Western blotting was performed as described in Dhugga, K. S. and Ray, P. M., Eur. J. Biochem. 220:943–953 (1994), but with a 1:100,000 dilution of the anti-RGP1 antiserum in TBSN buffer (50 mM Tris—Cl, pH 7.5/125 mM NaClIO0.3% Nonidet P-40).

Genomic DNA was isolated from pea stem tissue as described in Doyle, J. J. and Doyle J. L., Focus 12:13–15 (1990). Southern blot analysis was performed by the method of Athma and Peterson using cDNA as a probe. See Athma and Peterson, Genetics 128:163–174 (1991); Sambrook, et al., Molecular Cloning: A Laboratory Manual, Cold Springs Harbor Lab. Press, Plainview, N.Y. (1989). Northern blot analysis was carried out as described herein using whole cDNA as a probe. RNA was prepared using the RNeasy kit from Qiagen (Chatswirth, Calif.).

Gene Cloning

A pea cDNA library from mRNA from the subapial zone of 7–8 day-old etiolated pea seedling was constructed by Julie Palmer in Winslow Briggs' laboratory (Department of Plant Biology, Carnegie Institution of Washington, Stanford, Calif.). Sequences from this library were cloned into the expression vector uni-ZAP XR (Stratagene), between EcoRi and Xhol cloning sites. *E. coli* cells (XL-1 Blue, Stratagene) were plated with approximately 50,000 plaque-forming units of constructs per 150-mm plate and incubated at 42° C. for 4 hr. Nitrocellulose sheets (BA-S 85 m Schleicher & Schuell) treated with 10 mM isopropyl β-D-thiogalactoside and dried were laid over plaque-bearing plates, incubated at 37° C. for 4 hr, the blots removed, washed in TBSN, and developed as with Western blots but using 1:10,000 dilution of anti-RGP1 antiserum. Positive plaques were cored, vortexed in 50 mM tris-Ci (pH 7.5)110 mM MgCl2, kept on ice overnight, replated at a density of 200–300 plaque-forming units per 100-mm plate, and screened in the same way. Phage from positive plaques were subjected to in vivo excision as recommended by Stratagene. The phagemid-containing coli cells (SOLR strain, Statagene) were grown in terrific broth with 50 μg/ml ampicillin. DNA was prepared by the alkaline lysis method. See Sambrook, et al., *Molecular Cloning: A Laboratory Manual,* Cold Springs Harbor Lab. Press, Plainview, N.Y. (1989). Sequencing was performed by the Iowa State University Biomolecular Resource Center (Ames). Sequence analysis was performed with the Wisconsin Sequence Genetics Computer Group Analysis Package (GCG, Madison).

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. An isolated nucleic acid comprising a member selected from the group consisting of:

a) a polynucleotide that encodes a polypeptide of SEQ ID NO:2 or 4;

b) a polynucleotide encoding a maize Reversibly Glycosylated Protein (RGP) polypeptide;

c) a polynucleotide having at least 80% sequence identity to SEQ ID NO: 1 or at least 80% sequence identity to SEQ ID NO:3; wherein the percent sequence identity is based on the entire coding sequence and is determined by GAP under default parameters;

d) a polynucleotide which hybridizes under stringent hybridization conditions to a polynucleotide having the sequence set forth in SEQ ID NOS: 1 or 3, wherein the conditions include a wash with 0.1XS SC at 60 C.;

e) a polynucleotide comprising the sequence set forth in SEQ ID NOS: 1 or 3; and f) a polynucleotide complementary to the polynucleotide of any one of (a) through (e);

wherein the polynucleotide of (c), (d), or (f) each encode a monocot RGP polypeptide.

2. A vector comprising at least one nucleic acid of claim 1.

3. An expression cassette comprising at least one nucleic acid of claim 1 operably linked to a promoter, wherein the nucleic acid is in sense or antisense orientation.

4. A host cell into which is introduced at least one expression cassette of claim 3.

5. The host cell of claim 4 that is a plant cell.

6. A transgenic plant comprising at least one expression cassette of claim 3.

7. The transgenic plant of claim 6, wherein the plant is corn, soybean, sunflower, sorghum, canola, wheat, alfalfa, cotton, rice, barley, millet, Arabidopsis thaliana, tomato, Brassica vegetables, peppers, potatoes, apples, spinach, or lettuce.

8. A seed from the transgenic plant of claim 6.

9. The seed of claim 8, wherein the seed is from corn, soybean, sunflower, sorghum, canola, wheat, alfalfa, cotton, rice, barley, millet, Arabidopsis thaliana, tomato, Brassica vegetables, peppers, potatoes, apples, spinach, or lettuce.

10. The isolated nucleic acid of claim 1 which is a ribonucleic acid sequence.

11. A method for modulating the level of Reversibly Glycosylated Protein (RGP) polypeptide in a plant, comprising:

(a) stably transforming a plant cell with the polynucleotide of claim 1, operably linked to a promoter, wherein the polynucleotide is in sense or antisense orientation; and (b) growing the plant cell under plant growing conditions to produce a regenerated plant capable of expressing the polynucleotide for a time sufficient to modulate the level of RGP polypeptide in the plant.

12. The method of claim 11, wherein the plant is corn, soybean, sunflower, sorghum, canola, wheat, alfalfa, cotton, rice, barley, millet or Arabidopsis thaliana, tomato, Brassica vegetables, peppers, potatoes, apples, spinach, or lettuce.

13. The method of claim 11, wherein RGP is increased.

14. The method of claim 11, wherein RGP is decreased.

15. An isolated nucleic acid comprising a polynucleotide that encodes a polypeptide of SEQ ID NOS 2 or 4 or the complement of the polynucleotide.

16. An isolated nucleic acid comprising a polynucleotide amplified from a maize tissue nucleic acid library using the primers of SEQ ID NO: 5 and 6, or 7 and 8, wherein the polynucleotide encodes a maize RGP polypeptide, or the complement of the polynucleotide.

17. An isolated polynucleotide having at least 80% sequence identity to SEQ ID NO: 1 or at least 80% sequence identity to SEQ ID NO:3; wherein the percent sequence identity is based on the entire coding sequence and is determined by GAP under default parameters, wherein the polynucleotide encodes a monocot RGP polypeptide or the complement of the polynucleotide.

18. An isolated polynucleotide comprising the sequence set forth in SEQ ID NOS 1 or 3 or the complement thereof.

19. An isolated polynucleotide encoding a maize Reversibly Glycosylated Protein (RGP) polypeptide or the complement of the polynucleotide.

20. An isolated polynucleotide which hybridizes under stringent hybridization conditions to a polynucleotide having the sequence set forth in SEQ ID NOS: 1 or 3, wherein the conditions include a wash with 0.1XSSC at 60 C., wherein the polynucleotide encodes a monocot RGP polypeptide, or the complement of the isolated polynucleotide.

* * * * *

SEQUENCE LISTING

```
<160> NUMBER OF SEQ ID NOS: 9

<210> SEQ ID NO 1
<211> LENGTH: 1451
<212> TYPE: DNA
<213> ORGANISM: Zea mays
<220> FEATURE:
<221> NAME/KEY: CDS
<222> LOCATION: (100)...(1194)

<400> SEQUENCE: 1

ggcacgagca cctcccggtc cggcagcaga gagcgggggt gcagagagat cgagatccgg      60

aggccgcgag tgggagcgcc accaccagcg actgcggca atg gcg ggc acg gtg       114
                                           Met Ala Gly Thr Val
                                             1               5

acg gtc ccg ggg tcg tcg acc ccc tcc acg ccg ctg ctc aag gac gag      162
Thr Val Pro Gly Ser Ser Thr Pro Ser Thr Pro Leu Leu Lys Asp Glu
                 10                  15                  20

ctc gac atc gtg atc ccg acg atc cgc aac ctc gac ttc ctg gag atg      210
Leu Asp Ile Val Ile Pro Thr Ile Arg Asn Leu Asp Phe Leu Glu Met
             25                  30                  35

tgg cgg ccc ttc ttc cag ccc tac cac ctc atc atc gtg cag gac ggc      258
Trp Arg Pro Phe Phe Gln Pro Tyr His Leu Ile Ile Val Gln Asp Gly
         40                  45                  50

gac ccg acc aag acc atc aag gtg ccc gag ggc ttc gac tac gaa ctc      306
Asp Pro Thr Lys Thr Ile Lys Val Pro Glu Gly Phe Asp Tyr Glu Leu
     55                  60                  65

tac aac cgc aac gac atc aac cgc atc ctc ggg ccc aag gcc tcc tgc      354
Tyr Asn Arg Asn Asp Ile Asn Arg Ile Leu Gly Pro Lys Ala Ser Cys
 70                  75                  80                  85

atc tcc ttc aag gac tcc gcc tgc cgc tgc ttc ggc tac atg gtc tcc      402
Ile Ser Phe Lys Asp Ser Ala Cys Arg Cys Phe Gly Tyr Met Val Ser
                 90                  95                 100

aag aag aag tac atc tac acc atc gac gac gac tgc ttc gtt gcc aag      450
Lys Lys Lys Tyr Ile Tyr Thr Ile Asp Asp Asp Cys Phe Val Ala Lys
            105                 110                 115

gac cca tct ggc aag gat atc aat gct ctt gag cag cac atc aag aac      498
Asp Pro Ser Gly Lys Asp Ile Asn Ala Leu Glu Gln His Ile Lys Asn
        120                 125                 130

ctc ctc agc cca tcc acc ccg ttc ttc ttc aac acc ctg tac gac ccc      546
Leu Leu Ser Pro Ser Thr Pro Phe Phe Phe Asn Thr Leu Tyr Asp Pro
    135                 140                 145

tac cgt gag ggt gct gac ttt gtg cgt gga tac ccc ttc agc ctc agg      594
Tyr Arg Glu Gly Ala Asp Phe Val Arg Gly Tyr Pro Phe Ser Leu Arg
150                 155                 160                 165

gag ggt gct cac acc gcc gtc tcc cac ggc ctg tgg ctg aac atc cct      642
Glu Gly Ala His Thr Ala Val Ser His Gly Leu Trp Leu Asn Ile Pro
                170                 175                 180

gac tat gat gct ccc aca cag ctg gtc aag ccc aag gag agg aat gag      690
Asp Tyr Asp Ala Pro Thr Gln Leu Val Lys Pro Lys Glu Arg Asn Glu
            185                 190                 195

agg tat gtt gat gct gtc atg aca atc ccc aag gga acc ttg ttc ccc      738
Arg Tyr Val Asp Ala Val Met Thr Ile Pro Lys Gly Thr Leu Phe Pro
        200                 205                 210

atg tgt ggc atg aac ctt gcc ttc gac agg gat ctc att ggc cct gct      786
Met Cys Gly Met Asn Leu Ala Phe Asp Arg Asp Leu Ile Gly Pro Ala
    215                 220                 225

atg tac ttt ggt ctc atg ggt gat ggc cag ccc atc ggt cgc tac gac      834
Met Tyr Phe Gly Leu Met Gly Asp Gly Gln Pro Ile Gly Arg Tyr Asp
```

-continued

```
230                 235                 240                 245

gac atg tgg gca gga tgg tgt gtg aag gtc atc tgc gac cac ctg agc      882
Asp Met Trp Ala Gly Trp Cys Val Lys Val Ile Cys Asp His Leu Ser
                250                 255                 260

ctg gga gtc aag act ggc ctg cca tac atc tgg cac agc aag gct agc      930
Leu Gly Val Lys Thr Gly Leu Pro Tyr Ile Trp His Ser Lys Ala Ser
            265                 270                 275

aac ccc ttc gtt aac ttg aag aag gaa tac aag ggc atc ttc tgg cag      978
Asn Pro Phe Val Asn Leu Lys Lys Glu Tyr Lys Gly Ile Phe Trp Gln
        280                 285                 290

gag gac atc atc ccc ttc ttc cag aac gtg acc atc ccc aag gac tgc     1026
Glu Asp Ile Ile Pro Phe Phe Gln Asn Val Thr Ile Pro Lys Asp Cys
    295                 300                 305

gac acc gtc caa aag tgc tac atc tac ctc tct gga caa gtg aag gag     1074
Asp Thr Val Gln Lys Cys Tyr Ile Tyr Leu Ser Gly Gln Val Lys Glu
310                 315                 320                 325

aag ctg ggc acg att gac ccc tac ttt gtc aag ctc ggt gac gcc atg     1122
Lys Leu Gly Thr Ile Asp Pro Tyr Phe Val Lys Leu Gly Asp Ala Met
                330                 335                 340

gtc acc tgg atc gag gcc tgg gat gag ctg aac ccg tcg acc cct gcc     1170
Val Thr Trp Ile Glu Ala Trp Asp Glu Leu Asn Pro Ser Thr Pro Ala
            345                 350                 355

gcc gca aat ggc aag gcc aag tag atgtgccatc acttcggcac tggagtgaaa    1224
Ala Ala Asn Gly Lys Ala Lys
        360

aagaaagtat gattgggtcc tgcctaggcc ccatagatat agctcttttt tgagaaggaa   1284

gagagattaa ttcagcagca gcttttataa attctttgtt gtcatgaagc aggtggttct   1344

tttgtagttg atgaaaggga tttgtcgtcg ctatcgttta cataattcag acaataattt   1404

tatattgtgt aattctgaga atcaaagcac tgtttgtgtt atagcat                 1451


<210> SEQ ID NO 2
<211> LENGTH: 364
<212> TYPE: PRT
<213> ORGANISM: Zea mays

<400> SEQUENCE: 2

Met Ala Gly Thr Val Thr Val Pro Gly Ser Ser Thr Pro Ser Thr Pro
 1               5                  10                  15

Leu Leu Lys Asp Glu Leu Asp Ile Val Ile Pro Thr Ile Arg Asn Leu
            20                  25                  30

Asp Phe Leu Glu Met Trp Arg Pro Phe Phe Gln Pro Tyr His Leu Ile
        35                  40                  45

Ile Val Gln Asp Gly Asp Pro Thr Lys Thr Ile Lys Val Pro Glu Gly
    50                  55                  60

Phe Asp Tyr Glu Leu Tyr Asn Arg Asn Asp Ile Asn Arg Ile Leu Gly
65                  70                  75                  80

Pro Lys Ala Ser Cys Ile Ser Phe Lys Asp Ser Ala Cys Arg Cys Phe
                85                  90                  95

Gly Tyr Met Val Ser Lys Lys Lys Tyr Ile Tyr Thr Ile Asp Asp Asp
            100                 105                 110

Cys Phe Val Ala Lys Asp Pro Ser Gly Lys Asp Ile Asn Ala Leu Glu
        115                 120                 125

Gln His Ile Lys Asn Leu Leu Ser Pro Ser Thr Pro Phe Phe Phe Asn
    130                 135                 140

Thr Leu Tyr Asp Pro Tyr Arg Glu Gly Ala Asp Phe Val Arg Gly Tyr
145                 150                 155                 160
```

-continued

```
Pro Phe Ser Leu Arg Glu Gly Ala His Thr Ala Val Ser His Gly Leu
                165                 170                 175

Trp Leu Asn Ile Pro Asp Tyr Asp Ala Pro Thr Gln Leu Val Lys Pro
            180                 185                 190

Lys Glu Arg Asn Glu Arg Tyr Val Asp Ala Val Met Thr Ile Pro Lys
        195                 200                 205

Gly Thr Leu Phe Pro Met Cys Gly Met Asn Leu Ala Phe Asp Arg Asp
    210                 215                 220

Leu Ile Gly Pro Ala Met Tyr Phe Gly Leu Met Gly Asp Gly Gln Pro
225                 230                 235                 240

Ile Gly Arg Tyr Asp Asp Met Trp Ala Gly Trp Cys Val Lys Val Ile
                245                 250                 255

Cys Asp His Leu Ser Leu Gly Val Lys Thr Gly Leu Pro Tyr Ile Trp
            260                 265                 270

His Ser Lys Ala Ser Asn Pro Phe Val Asn Leu Lys Lys Glu Tyr Lys
        275                 280                 285

Gly Ile Phe Trp Gln Glu Asp Ile Ile Pro Phe Phe Gln Asn Val Thr
    290                 295                 300

Ile Pro Lys Asp Cys Asp Thr Val Gln Lys Cys Tyr Ile Tyr Leu Ser
305                 310                 315                 320

Gly Gln Val Lys Glu Lys Leu Gly Thr Ile Asp Pro Tyr Phe Val Lys
                325                 330                 335

Leu Gly Asp Ala Met Val Thr Trp Ile Glu Ala Trp Asp Glu Leu Asn
            340                 345                 350

Pro Ser Thr Pro Ala Ala Ala Asn Gly Lys Ala Lys
        355                 360

<210> SEQ ID NO 3
<211> LENGTH: 1827
<212> TYPE: DNA
<213> ORGANISM: Zea mays
<220> FEATURE:
<221> NAME/KEY: CDS
<222> LOCATION: (567)...(1616)

<400> SEQUENCE: 3

ccacgcgtcc gggaaacaag agggaaacgc cgtgagaggt cgccgatagg tgcgcgggtc      60

gcggtcgtcg cctcctctgc ctccctggca cttcggctcg gctcggcaaa cgcaacaaca     120

cggagcgggc gtggggagcg gagcggagcg gtgagcgagg atcgagggca acgtggcgag     180

gcacgcccga gggggagagg cgactttgct tccagttcca ggaaagagtg ggctataaaa     240

aggcgctcga gatccagatc tgggccgatg cgaccgccct cgctgctctc cctcaccctc     300

gacgccgcgc tcctccgcat cgccaatatc gccgacctct cccacctccc agaccacctc     360

ctcatcgacc tcttccgtag aaccctcagt gctggtaagc tgacagagaa agttctcaag     420

ttgtttctag caaccggctg tgaggatatc atattggctg ttcggttgct caacattaag     480

cagccactcg taccagtcct tcccacaagg tgctctgaga gattctagat ctgctgccgc     540

ccacatcgtt ttgattacct gagaag atg cct ttg gaa att caa gat agt gag      593
                             Met Pro Leu Glu Ile Gln Asp Ser Glu
                              1               5

gtt gac ata gtg att gcg gca ctc cag ccc aac ctg acc act ttc ttt      641
Val Asp Ile Val Ile Ala Ala Leu Gln Pro Asn Leu Thr Thr Phe Phe
 10                  15                  20                  25

gag gca tgg cga cca ttt ttc tcc cgt ttc cac atc att gtc gtc aaa      689
Glu Ala Trp Arg Pro Phe Phe Ser Arg Phe His Ile Ile Val Val Lys
```

-continued

```
                 30                  35                  40

gat cca gac atg gca gag gat ctt caa atc cct gca ggt ttt gat ctc      737
Asp Pro Asp Met Ala Glu Asp Leu Gln Ile Pro Ala Gly Phe Asp Leu
             45                  50                  55

aag gtt tac acc aag tca gat att aat ggg ttg ctt ggt gcc tcc tca      785
Lys Val Tyr Thr Lys Ser Asp Ile Asn Gly Leu Leu Gly Ala Ser Ser
         60                  65                  70

tcc ata aac tta tct ggt cac tca tgc cgt tac ttt ggg tat ctt gtc      833
Ser Ile Asn Leu Ser Gly His Ser Cys Arg Tyr Phe Gly Tyr Leu Val
     75                  80                  85

tca cgc aag aag tat gtg att tca gtt gat gac aat tgc ctc cca gcg      881
Ser Arg Lys Lys Tyr Val Ile Ser Val Asp Asp Asn Cys Leu Pro Ala
 90                  95                 100                 105

aag gac act gct ggg tcg act gtt gat gtt gtt gca cag cac atg gcc      929
Lys Asp Thr Ala Gly Ser Thr Val Asp Val Val Ala Gln His Met Ala
                110                 115                 120

aat ctg aaa aca cct gct aca cct ttc ttt ttc aac aca ctc tat gat      977
Asn Leu Lys Thr Pro Ala Thr Pro Phe Phe Phe Asn Thr Leu Tyr Asp
            125                 130                 135

cca tac agg aaa ggt gct gac ttt gtc cgt ggt tac cca ttc agc ctg     1025
Pro Tyr Arg Lys Gly Ala Asp Phe Val Arg Gly Tyr Pro Phe Ser Leu
        140                 145                 150

cgt gag ggg gtt gag tgc atg ctc tcg tgt ggt ttg tgg ctt cat aat     1073
Arg Glu Gly Val Glu Cys Met Leu Ser Cys Gly Leu Trp Leu His Asn
    155                 160                 165

gct gac tac gac ccg atg act cat gtt gtg aag aga aat caa cgg aac     1121
Ala Asp Tyr Asp Pro Met Thr His Val Val Lys Arg Asn Gln Arg Asn
170                 175                 180                 185

aca aca tat gtg gat gct gtg atg acg gtt ccg ctt ggt gcc atg ctg     1169
Thr Thr Tyr Val Asp Ala Val Met Thr Val Pro Leu Gly Ala Met Leu
                190                 195                 200

cct gtg agc ggg ata aat gtt gca ttc aac cgc gat gtg ctg ggg cct     1217
Pro Val Ser Gly Ile Asn Val Ala Phe Asn Arg Asp Val Leu Gly Pro
            205                 210                 215

gct atg ttc cca ggc ctg cgt cta aga aac gaa ggg aag cac aga tgg     1265
Ala Met Phe Pro Gly Leu Arg Leu Arg Asn Glu Gly Lys His Arg Trp
        220                 225                 230

gat acc ctt gaa gac ata tgg aat ggc tta tgt gct aaa gta gtc tgc     1313
Asp Thr Leu Glu Asp Ile Trp Asn Gly Leu Cys Ala Lys Val Val Cys
    235                 240                 245

gac agc ttg gga tat ggt gtg aag acc gga ctg cct tat gtg atg aga     1361
Asp Ser Leu Gly Tyr Gly Val Lys Thr Gly Leu Pro Tyr Val Met Arg
250                 255                 260                 265

agt gat gca gaa gca ggt aaa gct ctg gag agc ttg aaa gag tgg gaa     1409
Ser Asp Ala Glu Ala Gly Lys Ala Leu Glu Ser Leu Lys Glu Trp Glu
                270                 275                 280

ggg gta aaa gtc atg gac gat gtt ctc cca ttc ttc cag tcg ctc aag     1457
Gly Val Lys Val Met Asp Asp Val Leu Pro Phe Phe Gln Ser Leu Lys
            285                 290                 295

cta tcg agg act gca gtt act gtt gac gat tgt gtt aag gag ctt gct     1505
Leu Ser Arg Thr Ala Val Thr Val Asp Asp Cys Val Lys Glu Leu Ala
        300                 305                 310

gga att gtc cgt gag aaa cta gga cct aag aat gca atc ttc acc aaa     1553
Gly Ile Val Arg Glu Lys Leu Gly Pro Lys Asn Ala Ile Phe Thr Lys
    315                 320                 325

gca gcc gat gcc atg gtg gaa tgg aac aat ctc tgg aaa gtg cat ggt     1601
Ala Ala Asp Ala Met Val Glu Trp Asn Asn Leu Trp Lys Val His Gly
330                 335                 340                 345

gct cag aat gca tag tttgggaatt tgcatgtttc ctacagagca tctaatagtt     1656
```

```
Ala Gln Asn Ala

gtttggagtg cgcgttttac agttctaaat tttccctgtg gaactcatga agctgaaata   1716

aacaacagtc ctttatgccg tgaatttggc atgaatagct gagcatctca ttgtatacgc   1776

ttaagaatta tgtaatgtaa tgcatcaaaa gaacatgtga tgttttcttg c            1827


<210> SEQ ID NO 4
<211> LENGTH: 349
<212> TYPE: PRT
<213> ORGANISM: Zea mays

<400> SEQUENCE: 4

Met Pro Leu Glu Ile Gln Asp Ser Glu Val Asp Ile Val Ile Ala Ala
 1               5                  10                  15

Leu Gln Pro Asn Leu Thr Thr Phe Phe Glu Ala Trp Arg Pro Phe Phe
            20                  25                  30

Ser Arg Phe His Ile Ile Val Val Lys Asp Pro Asp Met Ala Glu Asp
        35                  40                  45

Leu Gln Ile Pro Ala Gly Phe Asp Leu Lys Val Tyr Thr Lys Ser Asp
    50                  55                  60

Ile Asn Gly Leu Leu Gly Ala Ser Ser Ser Ile Asn Leu Ser Gly His
65                  70                  75                  80

Ser Cys Arg Tyr Phe Gly Tyr Leu Val Ser Arg Lys Lys Tyr Val Ile
                85                  90                  95

Ser Val Asp Asp Asn Cys Leu Pro Ala Lys Asp Thr Ala Gly Ser Thr
            100                 105                 110

Val Asp Val Val Ala Gln His Met Ala Asn Leu Lys Thr Pro Ala Thr
        115                 120                 125

Pro Phe Phe Phe Asn Thr Leu Tyr Asp Pro Tyr Arg Lys Gly Ala Asp
    130                 135                 140

Phe Val Arg Gly Tyr Pro Phe Ser Leu Arg Glu Gly Val Glu Cys Met
145                 150                 155                 160

Leu Ser Cys Gly Leu Trp Leu His Asn Ala Asp Tyr Asp Pro Met Thr
                165                 170                 175

His Val Val Lys Arg Asn Gln Arg Asn Thr Thr Tyr Val Asp Ala Val
            180                 185                 190

Met Thr Val Pro Leu Gly Ala Met Leu Pro Val Ser Gly Ile Asn Val
        195                 200                 205

Ala Phe Asn Arg Asp Val Leu Gly Pro Ala Met Phe Pro Gly Leu Arg
    210                 215                 220

Leu Arg Asn Glu Gly Lys His Arg Trp Asp Thr Leu Glu Asp Ile Trp
225                 230                 235                 240

Asn Gly Leu Cys Ala Lys Val Val Cys Asp Ser Leu Gly Tyr Gly Val
                245                 250                 255

Lys Thr Gly Leu Pro Tyr Val Met Arg Ser Asp Ala Glu Ala Gly Lys
            260                 265                 270

Ala Leu Glu Ser Leu Lys Glu Trp Glu Gly Val Lys Val Met Asp Asp
        275                 280                 285

Val Leu Pro Phe Phe Gln Ser Leu Lys Leu Ser Arg Thr Ala Val Thr
    290                 295                 300

Val Asp Asp Cys Val Lys Glu Leu Ala Gly Ile Val Arg Glu Lys Leu
305                 310                 315                 320

Gly Pro Lys Asn Ala Ile Phe Thr Lys Ala Ala Asp Ala Met Val Glu
                325                 330                 335
```

-continued

```
Trp Asn Asn Leu Trp Lys Val His Gly Ala Gln Asn Ala
            340                 345


<210> SEQ ID NO 5
<211> LENGTH: 28
<212> TYPE: DNA
<213> ORGANISM: Zea mays

<400> SEQUENCE: 5

tcttgagcag cacatcaaga acctcctc                                          28


<210> SEQ ID NO 6
<211> LENGTH: 27
<212> TYPE: DNA
<213> ORGANISM: Zea mays

<400> SEQUENCE: 6

tgccgaagtg atggcacatc tacttgg                                           27


<210> SEQ ID NO 7
<211> LENGTH: 29
<212> TYPE: DNA
<213> ORGANISM: Zea mays

<400> SEQUENCE: 7

cagacatggc agaggatctt caaatccct                                         29


<210> SEQ ID NO 8
<211> LENGTH: 26
<212> TYPE: DNA
<213> ORGANISM: Zea mays

<400> SEQUENCE: 8

tgcagtcctc gatagcttga gcgact                                            26


<210> SEQ ID NO 9
<211> LENGTH: 32
<212> TYPE: DNA
<213> ORGANISM: Zea mays

<400> SEQUENCE: 9

agagaagcca acgccawcgc ctcyatttcg tc                                     32
```